US009877809B2

(12) United States Patent
Hanisch et al.

(10) Patent No.: US 9,877,809 B2
(45) Date of Patent: Jan. 30, 2018

(54) ABUTMENT SYSTEM FOR IMMEDIATE IMPLANTS FOR PRODUCING A DENTAL PROSTHESIS

(71) Applicant: OLISTA AG, Kuesnacht (CH)

(72) Inventors: Oliver Hanisch, Paris (FR); Stefan Paul, Zurich (CH)

(73) Assignee: OLISTA AG, Erlenbach ZH (CH)

(*) Notice: Subject to any disclaimer, the term of this patent is extended or adjusted under 35 U.S.C. 154(b) by 40 days.

(21) Appl. No.: 14/416,485

(22) PCT Filed: Jul. 22, 2013

(86) PCT No.: PCT/EP2013/065406
§ 371 (c)(1),
(2) Date: Jan. 22, 2015

(87) PCT Pub. No.: WO2014/016244
PCT Pub. Date: Jan. 30, 2014

(65) Prior Publication Data
US 2015/0182312 A1    Jul. 2, 2015

(30) Foreign Application Priority Data

Jul. 23, 2012 (EP) .................... 12177460

(51) Int. Cl.
*A61C 8/00* (2006.01)

(52) U.S. Cl.
CPC ............ *A61C 8/0066* (2013.01); *A61C 8/005* (2013.01); *A61C 8/0022* (2013.01); *A61C 8/0074* (2013.01); *A61C 8/0077* (2013.01)

(58) Field of Classification Search
CPC ..... A61C 8/005; A61C 8/0051; A61C 8/0077; A61C 8/0066; A61C 8/0022; A61C 8/0074

(Continued)

(56) References Cited

U.S. PATENT DOCUMENTS 4,960,381 A   10/1990 Niznick
5,110,292 A    5/1992 Balfour
(Continued)

FOREIGN PATENT DOCUMENTS

EP    1 205 158      4/2005
JP    2008-149121    7/2008
(Continued)

OTHER PUBLICATIONS

PCT Search Report and Written Opinion issued in PCT/EP2013/065406 dated Oct. 4, 2013.

*Primary Examiner* — Nicholas Lucchesi
(74) *Attorney, Agent, or Firm* — Greenblum & Bernstein, P.L.C.

(57) ABSTRACT

The invention relates to an abutment system (200) for use in the area of the front teeth and premolars, with an abutment base (102) which comprises a first interface (107) for placement on an implant and a second interface (123) for fixing a crown or suprastructure. The abutment base (102) has a scalloped top side (104) and the implant defines an implant axis (AI). The abutment base (102) has a three-dimensional shape which is designed asymmetrically relative to the implant axis (AI). Moreover, it has a lateral surface region (111) which has a concave shape when viewed in a vertical section. Additionally, the abutment system (200) comprises a separate prosthetic post (210) which can be fixed in the area of the scalloped top side (104) of the abutment base (102), wherein the prosthetic post (210) extends coaxially to the implant axis (AI) when fixed.

20 Claims, 9 Drawing Sheets

(58) Field of Classification Search
USPC .................................................. 433/173, 174
See application file for complete search history.

(56) References Cited

U.S. PATENT DOCUMENTS

| | | | |
|---|---|---|---|
| 5,209,666 A | 5/1993 | Balfour | |
| 5,407,359 A | 4/1995 | Balfour | |
| 5,417,568 A * | 5/1995 | Giglio | A61C 8/005 433/172 |
| 5,810,592 A * | 9/1998 | Daftary | A61C 8/005 433/172 |
| 6,174,167 B1 | 1/2001 | Wohrle | |
| 2004/0121286 A1 * | 6/2004 | Aravena | A61C 8/0006 433/173 |
| 2005/0214714 A1 * | 9/2005 | Wohrle | A61C 8/0018 433/173 |
| 2005/0266381 A1 * | 12/2005 | Abarno | A61C 1/084 433/173 |
| 2006/0199150 A1 * | 9/2006 | Niznick | A61C 8/0022 433/173 |
| 2006/0286508 A1 | 12/2006 | Bassett | |
| 2007/0031792 A1 * | 2/2007 | Casement | A61C 8/0048 433/218 |
| 2007/0031793 A1 * | 2/2007 | Casement | A61C 8/0048 433/218 |
| 2009/0239195 A1 | 9/2009 | Wohrle | |
| 2014/0205969 A1 * | 7/2014 | Marlin | A61C 8/0001 433/173 |

FOREIGN PATENT DOCUMENTS

| | | |
|---|---|---|
| WO | WO 2004/037110 | 5/2004 |
| WO | WO 2006/138351 | 12/2006 |

* cited by examiner

ABUTMENT SYSTEM FOR IMMEDIATE IMPLANTS FOR PRODUCING A DENTAL PROSTHESIS

The invention concerns an abutment system for establishing an implant-supported dental prosthesis. In particular, abutment systems for single implants are concerned which are applied in the area of frontal row of teeth or premolars.

STATE OF THE ART

It is known that one may have lost or extracted teeth replaced by implant-supported dental prosthesis. So-called osseointegrated implants are employed for more than 40 years. In case of a skillfully handled osseointegration a stable implant-bone composition results. In case of posterior arranged teeth the restauration primarily concerns the preservation or the reconstruction of the chewing function. In the visible area, however, also the aesthetics and in particular the preservation of the soft tissue are concerned.

FIG. 1A shows a schematic frontal view of two human anterior teeth FZ: 21 and FZ: 11 together with the surrounding gingiva. A first vertical section through one of the anterior teeth FZ: 11 and the surrounding structures are shown in an oversimplified form in FIG. 1B. A second vertical section through the same anterior tooth FZ: 11 is shown in FIG. 1A, wherein the second vertical section is perpendicular with respect to the first vertical section.

Essential terms are being explained in connection with FIGS. 1A through 1C since in the following reference is made repeatedly to the anatomy of teeth.

The tooth FZ as such is composed of dentin 11 and it is surrounded in the upper (mostly visible) area by dental enamel 7. The respective cemento-enamel junction SZG typically has scalloped shape, as indicated in FIG. 1B.

The root of the tooth 12 sits in an alveolus of the jawbones 5. If viewed from the outside to the inner side the so-called gingiva (epithel) 9 sits on the connective tissue 6. Collagen fibers 14 are arranged inside the connective tissue 6. On the top left some of these collagen fibers 14 are indicated in FIGS. 1B and 1C. The fibers 14 surround the tooth FZ in a ring or loop shape (if viewed from the top). The parodont 13 is situated between the jawbone 5 and root of the tooth 12 which consists of root dentin. The root dentin on the outer side is covered by a thin layer of root cement. The nerve 8 sits inside the tooth FZ.

In FIG. 2A a strongly schematized section of a molar tooth BZ: 16 and a premolar PM: 15 of an upper jaw of a human denture including the surrounding soft tissue morphology right underneath the cemento-enamel junction SZG is shown as example. One can see the gingiva 9 and the connective tissue 6 in FIG. 2A. The orientation of the collagen fibers 14 in the connective tissue 6 is indicated by lines/curves, whereby the collagen fibers 14 enclose the two teeth BZ and PM in a ring- or loop shape and insert on the root surface, too. Inside the two teeth BZ and PM one can see in the section the internal channel of the nerve 8 and the surrounding root dentin of the root of the tooth 12. A thin layer of the root cement is located on the outside on the root dentin of the root of the tooth 12, which is not separately illustrated here.

FIG. 2B shows as an example a schematic view of the upper jaw of a human denture from the bottom.

After the loss or the extraction of a tooth FZ in the frontal area of the jaw and the insertion of an implant, sometimes the reduction of the gingiva 9 and/or jawbone 5 can be determined already after a short period. In this context it matters whether the implant was inserted with a time delay or whether it was implanted in the context of an immediately placed implant right after the extraction of the tooth FZ. One can assume that the connective tissue 6 and the contour/structure of the enveloping collagen fibers 14 are still sound if the tooth FZ is still in place and if an extraction is for instance advisable because of a local infection or a trauma. The immediate insertion of the implant into the extraction alveolus and the insertion of a provisional restauration can be advantageous in this case. These so-called immediate-immediate techniques are thus gaining in importance for the insertion of dental implants although until now the delayed-immediate approach is the most widely used implant technology.

The implant is completely situated epi- or subcrestal in case of a classic tooth replacement implant. The old school until today prevails that dental implants have to be inserted so that the upper edge of the implant is situated at or (only a little) underneath the upper most level KN1 of the surrounding bones (see for instance FIG. 1C) of the jawbone 5. This is inter alia justified by the desire to prevent in any case a recession of the bones 5 and the soft tissue 6, 9 and that the upper edge of the implant becomes visible.

Different strongly schematized views of a prior known implant 1 and abutment 2 are shown in FIGS. 3A through 3C as schematic diagrams. Typically an abutment 2 is employed as intermediate element between a supra construction and/or crown and the implant 1, as shown by means of the FIGS. 3A through 3C in a strongly schematized form. Making reference the FIG. 1B, the abutment 2 typically sits in the region of the penetration point through the soft tissue (connective tissue 6 and ephitel 9), where the interface between the implant and abutment lie epi- or subcrestal, depending on the height where the implant was situated.

Until now abutments 2 are often employed which have rotationally symmetric basic shape. However, such abutments 2 due to their rotationally symmetric basic shape inter alia have the disadvantage that they cannot be integrated into a tooth row in an optimum position and that thus the production of the supra construction is made difficult and in some cases even impossible, since natural anterior (FZ) and premolar (PM) teeth in the region of the cemento-enamel junction SZG have a deltoid respectively oval root cross-section. An adaptation (grinding) inside the patient's mouth is almost impossible because of the hard material of the abutment 2. Such problems, however, do not exist in case of abutments individually produced in a laboratory. This, however, results in a high cost and time effort.

As can be seen in FIGS. 3A and 3C, the abutments 2 so far often have a flat upper side 3. As of late, there are some abutments 2 with a so-called scalloped (rolling or saddle-shaped) upper surface 4, as can be seen in FIG. 4. In case of this known solution the scalloped upper surface 4 approximately assumes the shape of a natural cemento-enamel junction SZG of the tooth FZ, which was extracted before.

There already exists a scalloped implant 10, which is schematically illustrated in FIG. 4, and which is being offered by the Noble Biocare company, Sweden, using the name NobelPerfect™. This concerns a one-piece implant 10 where the implant 1 as such and the abutment 2 are implemented as one piece. The NobelPerfect™ implant 10 is rotationally symmetric with respect to the implant axis AI, as can be seen in FIG. 4. The abutment section 2 of the implant 10 is rotationally symmetric, too, and it has a hat shape. Details of such a scalloped implant 10 can for instance be derived from U.S. Pat. No. 6,174,167 B1. In this letters patent U.S. Pat. No. 6,174,167 B1 an implant is described comprising a scalloped surface with bulges and depressions so as to reproduce the physiological contour of the natural bone-tissue-morphology.

A further implant is known from the European patent application EP 1205158 A1, the shape of which is adapted to the differences in the level of the progression of the jawbone. In accordance with this patent application the implant is widened at its distal end at opposite areas. This implant shows an inner recess which is shaped in accordance with the widening. That is, the implant is hollow at least in the upper area. A respectively shaped platform body, which serves as abutment, can be inserted into this recess. The interface between implant and abutment are inside.

It is a disadvantage of this solution that the implant as such in some way has to be adapted to the level difference in the progression of the Jawbone. The implant thus has to be inserted exactly so that its widening with respect to the progression of the jawbone assumes an optimum position. The implant is not standing in the optimum position if it is not screwed in far enough or too far.

It is an object to provide an abutment system and an implant constructed there upon which facilitate/s an implantation procedure where no or only a marginally small recession at the gingiva and/or jawbone occurs. Furthermore, aesthetically appealing and durable tooth replacement solutions shall be facilitated first of all for anterior and premolar teeth.

In accordance with the invention an abutment system is concerned for use in the region of anterior and premolar teeth with a standard abutment basis having a first interface for attaching onto a (standard-) implant and a second interface for fixing a prosthetic element (e.g. a crown or supra construction), whereby the abutment basis comprises a scalloped upper surface. In principle, the abutment system of the invention is independent of the interface between the (standard-) implant and the abutment. The abutment system of the invention can be adapted to nearly all interfaces.

After the insertion the implant defines a so-called implant axis. The abutment system of the invention is characterized in that the abutment basis has a three-dimensional shape not being symmetrical with respect to this implant axis, that is the three-dimensional shape of the abutment basis thus is not a body of rotation. Furthermore, the abutment basis has a envelop area which, if viewed in a vertical section, has a concave shape. The abutment system comprises in addition to the abutment basis a separate prosthetic post which can be fixed in the region of the scalloped upper surface of the abutment basis so that prosthetic post is extending in the faxed state coaxially with respect to the implant axis.

The abutment basis of all embodiments has a three-dimensional asymmetric shape which is designed to essentially approximate in the mesial, distal, vestibular and palatial direction the shape of the cemento-enamel junction SZG. The abutment basis of the invention thus is also referred to as anatomically shaped abutment basis.

The abutment basis of all embodiments has a three-dimensional concave envelop area which provides for a smooth transition between a rotationally symmetric interface surface (in the region of the first interface) and a non-symmetric, circumferential ridge/shoulder respectively a non-symmetric, scalloped surface.

The concave envelop area provides some kind of a waist of the abutment basis along the progression of the scalloped cemento-enamel junction SZG which leads to a better integration into the surrounding tissue structure.

Abutment basis are primarily concerned which are fixed on implants after these have been inserted into the bone of the upper- or lower jaw. A removable or basisfixed dental prosthesis can be anchored on or at these abutment basis. In accordance with the invention the fixing of the dental prosthesis occurs by means of a prosthetic post, which is carried out separately from the respective abutment basis.

In particular the so-called immediate implantation is herein concerned where immediately or delayed after the extraction of a tooth or tooth remainder the implant is implanted in the bone of the upper- or lower jaw and an abutment basis is attached thereon.

In accordance with the invention, the immediate implantation is preferred to preserve the soft tissue morphology in case of single tooth implants. In particular the preservation of the gingival situation is concerned by employing a special abutment system which for instance is fixed on a commercially available implant that is a two-piece abutment system is concerned.

The invention in particular concerns the so-called soft tissue integration of the anatomically shaped abutment basis.

Implants are suited for all embodiments with a base body which has a parallel wall or root-shaped (conical) configuration and which has a rotationally symmetric shape relative to a central axis of rotation, which coincides with the implant axis. Currently, so-called screw implants (screw-type implants) are preferably used. Such screw implants—but other standard implants as well—can be used in connection with the present invention. The implant thereby serves as anchoring element in the jawbone.

In accordance with the invention, the abutment bass is seated so that the upper edge is positioned supracrestally. Preferably (but not exclusively) the upper edge of the abutment basis is positioned ≥21 mm above the bone ridge of the alveolus of the extracted tooth. An implantation method is preferred in particular where the upper edge is positioned circularly about 1.5 mm above the jawbone.

An element/component premachined in series serves as so-called abutment basis, which is employed as connecting element between the implant and a supra construction or crown. Three or four different types/shapes of abutment basis can be provided in accordance with the invention in order to account for the different shapes of anterior and premolar teeth.

The abutment basis of the invention can be produced in specialized fabrication plants in highest quality, keeping the shape and with endurable materials. The endurable materials can be picked taking into consideration the keeping of the shape and the body compatibility. A machining of the abutment basis is not required. Therefore, particularly titanium, titanium alloys and zircon oxide are suitable as material for the abutment basis.

Pursuant to the invention at least one mass-produced abutment basis is employed. The mentioned supra construction or crown, however, are in most cases produced individually per patient.

In accordance with the invention the abutment basis might be connected to the implant for instance via a polygonal interface. Depending on the implementation the polygonal interface enables three or more than three angular positions (index positioning) of the abutment basis with respect to the implant. Due to this one gains additional degrees of freedom enabling an optimum alignment of the mass-produced, scalloped abutment basis relative to the bone and tissue structures.

The employment of an implant-abutment restauration unit (here altogether called implant system) in accordance with the invention offers results which are aesthetically very appealing since in the first instance no or only very small recessions are to be observed in the marginal soft tissue.

Gingival tissue structures and the contour thereof can be preserved as far as possible by the invention, which inter alia causes a fast incorporation and a stable anchoring.

Further advantageous embodiments can be taken from the dependent claims.

DRAWINGS

Embodiments of the invention are going to be described in more detail in the following by making reference to the drawings.

DETAILED DESCRIPTION

Terms are used in conjunction with the present description which are also used in relevant publications and patents. However, it is to be noted that the use of these terms is only to serve for better understanding. The ideas of the invention and the scope of protection of the patent claims are not to be restricted in the interpretation thereof by the specific selection of the terms. The invention may readily be transferred to other term systems and/or technical fields. The terms are to be applied accordingly in other technical fields.

Figure 5A:
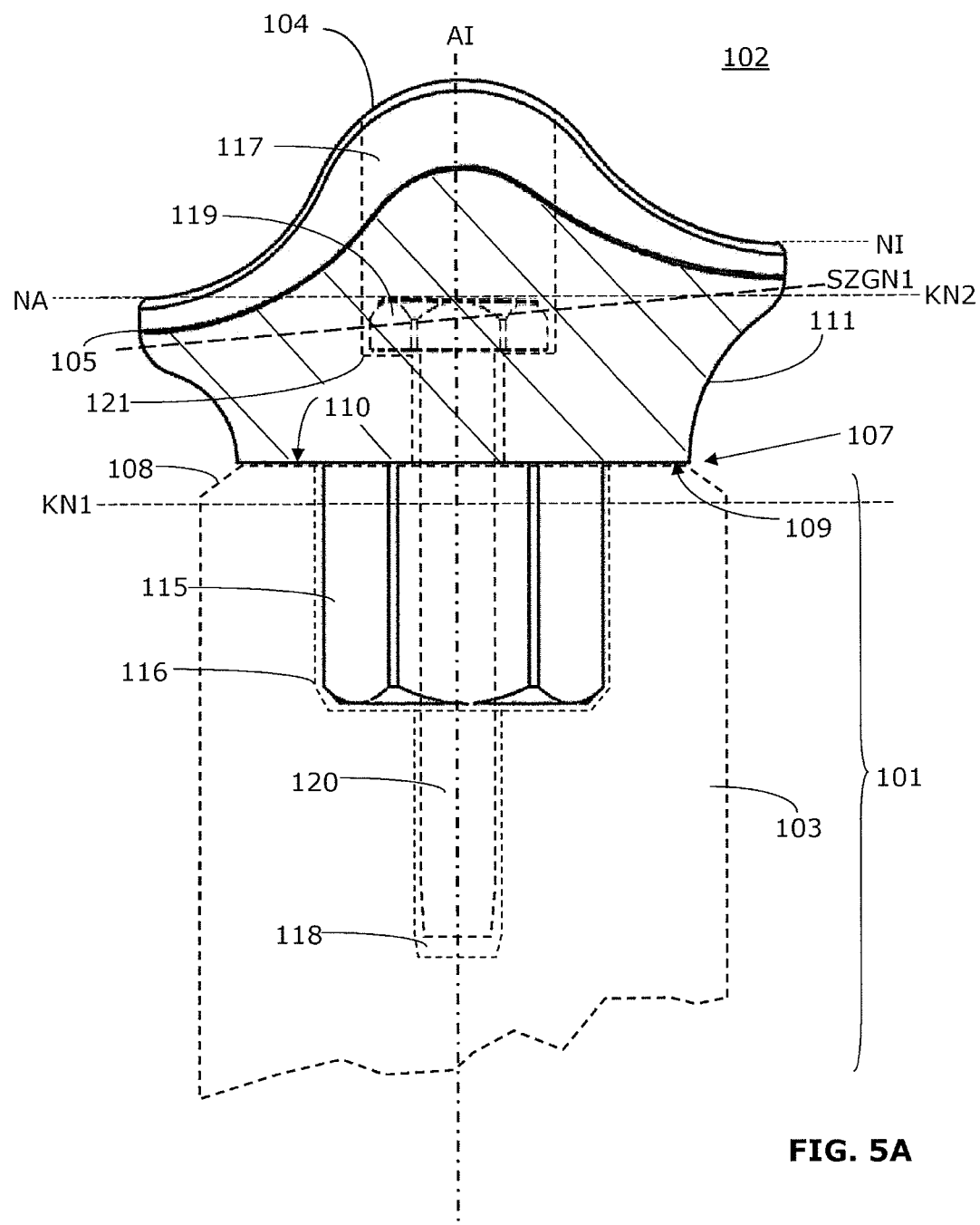
FIG. 5A shows a side view of a first abutment basis of the invention in mesial direction (similar to the viewing direction in FIG. 1B), wherein the position and shape of a fitting exemplary implant is indicated by means of dashed contour lines.
Figure 5B:
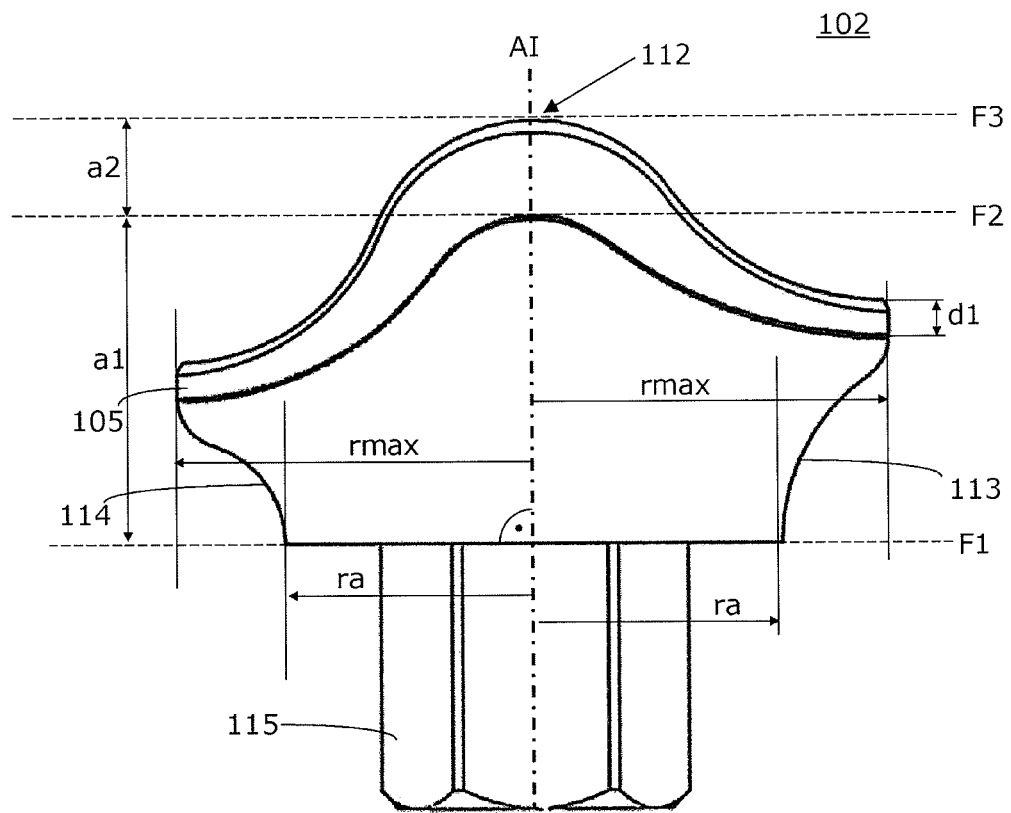
FIG. 5B shows the same side view of the first abutment basis of FIG. 5A, wherein reference lines are drawn.
Figure 5C:
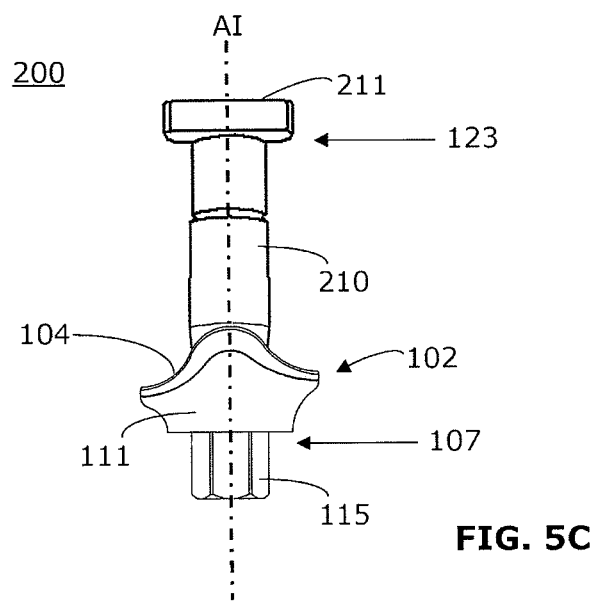
FIG. 5C shows a miniaturized side view of the first abutment basis of FIG. 5A together with a prosthetic post viewed in mesial direction.

In accordance with the invention, an abutment system 200 (see for instance FIG. 5C) is concerned which is primarily designed for use in the region of the anterior and premolar teeth. The abutment system 200 comprises an abutment basis 102. An exemplary abutment basis 102 is shown in the FIGS. 5A through 5D. The abutment basis 102 comprises a first interface 107, which is designed for the attachment on an implant 103, as is for instance indicated in FIG. 5A. The implant 103 defines after the insertion by the position of its implant axis AI the position of all further elements (such as abutment basis 102, prosthetic post 210 and restauration elements), which are fixed at respectively on the implant 103, as indicated in FIG. 5C. The abutment system 200 comprises a second interface 123 in addition to the first interface 107 for the attachment of the restauration elements (e.g. a crown or supra construction).

The abutment basis 102 of all embodiments of the invention comprises a scalloped upper surface 104 and it has a three-dimensional shape which is not designed symmetrically with respect to the implant axis AI. Furthermore, the abutment basis 102 is enclosed by a cladding area 111 which has a concave form viewed in the vertical section. In FIGS. 5A and 5B for instance, one can see the concave form of the cladding area 111 well.

The abutment system 200 of all embodiments comprises in addition a separate prosthetic post 210 which can be attached in the region of the scalloped upper surface 104 of the abutment basis 102 so that the prosthetic post 210 in the fixed state extends coaxially with respect to the implant axis AI. An exemplary abutment system 200 with abutment basis 102 and prosthetic post 210 is shown in FIG. 5C.

Figure 5D:
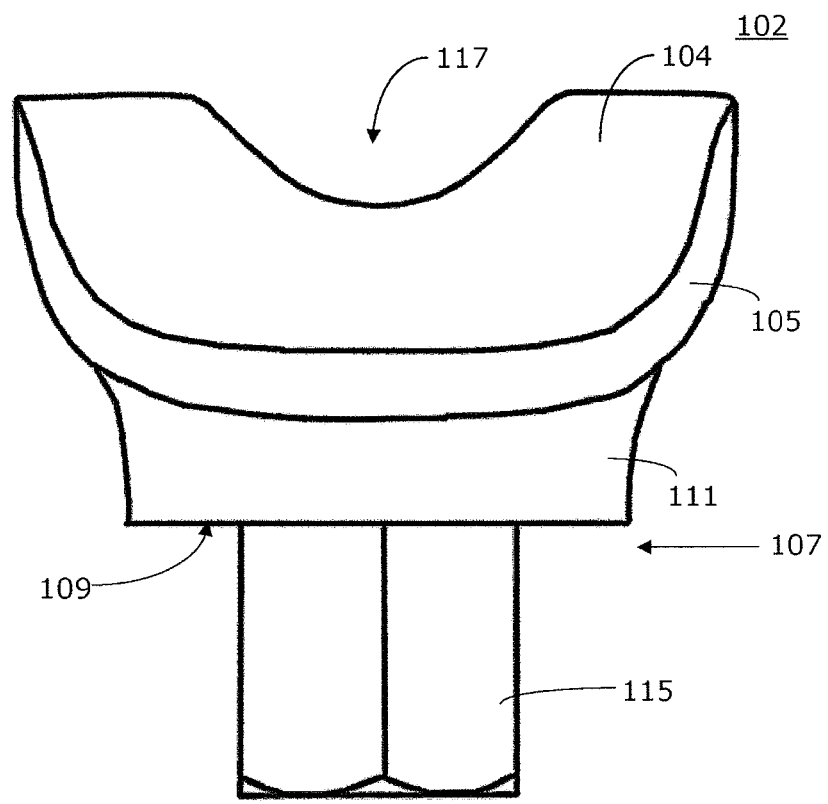
FIG. 5D shows a side view of the first abutment basis of the invention viewed in palatine direction.
Figure 6A:
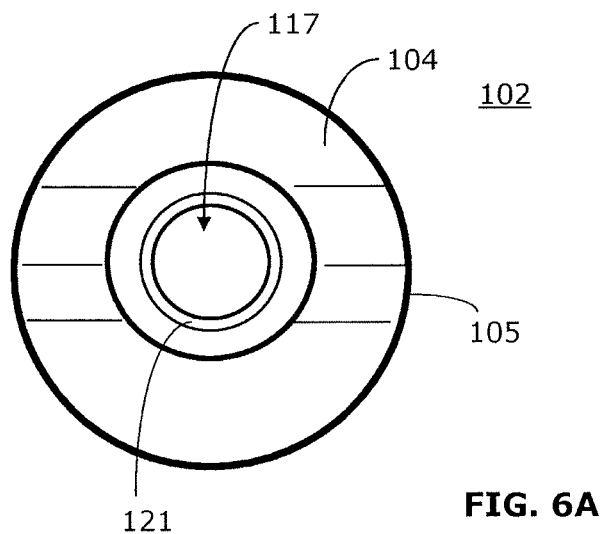
FIG. 6A shows a strongly schematized top view of a further abutment basis of the invention which has a slightly deltoid foot print.

Preferably, the abutment basis 102 of all embodiments comprises a proximal interface plane 109 in the region of the first interface 107, which essentially is flat and stands perpendicularly with respect to the implant axis AI. Furthermore, the abutment basis 102 of all embodiments preferably comprises a through hole 117 in the region of the scalloped upper surface 104 which serves for the attachment of the prosthetic post 210 and/or for connecting it with the implant 103. The position of the through hole 117 can be seen in FIG. 5D in outlines. The through hole 117 of another inventive abutment basis 102 is shown in FIG. 6A in a top view.

In accordance with the invention that cross-sectional shape (in the vertical section through the abutment basis 102) is asymmetrical, as is presented in the following.

Figure 1A:
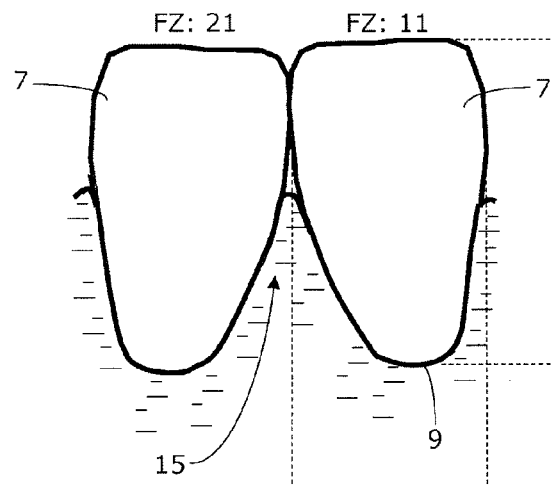
FIG. 1A shows a schematic frontal view of two human anterior teeth including the surrounding gingiva.
Figure 1B:
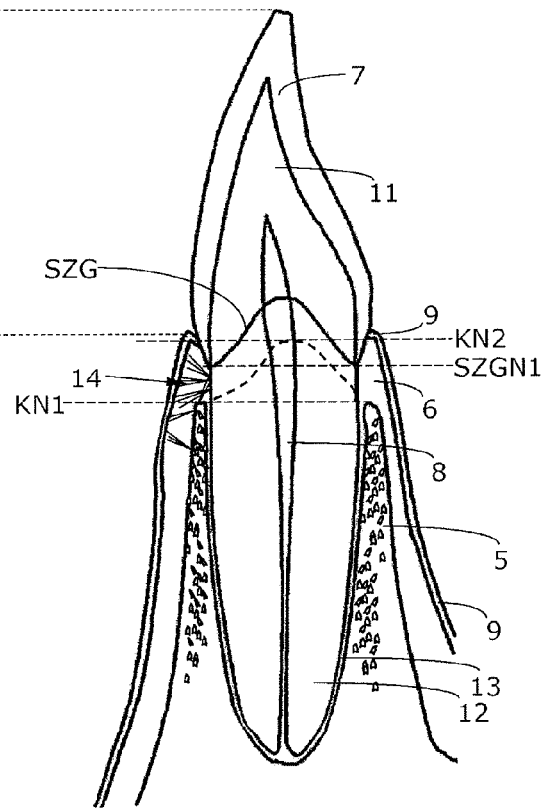
FIG. 1B shows a strongly schematized sectional view in mesial direction of the right hand anterior tooth of FIG. 1A including the surrounding soft tissue and bone morphology.
Figure 1C:
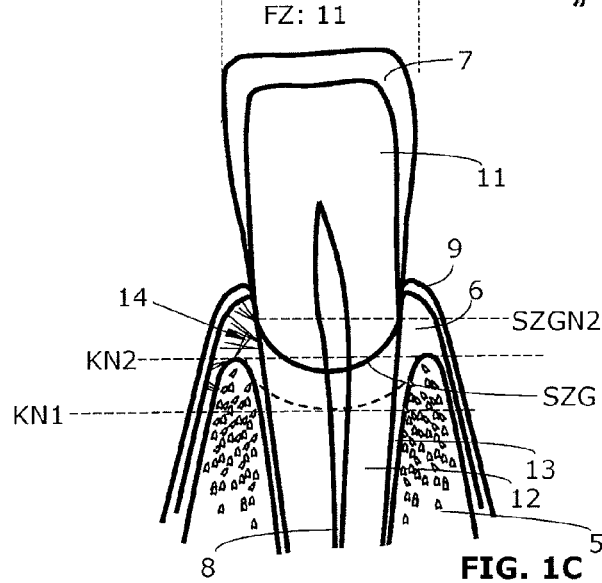
FIG. 1C shows a strongly schematized sectional view in palatine direction of the right hand anterior tooth of FIG. 1A including the surrounding soft tissue and bone morphology.

In case of an anterior tooth FZ, for instance, the cemento-enamel junction SZGN2 on the right hand and left hand side of the tooth FZ: 11 can lie at about the same height, as indicated in FIG. 1C. The progression of the cemento-enamel junction SZG follows at the front of the tooth (on the left in FIG. 1B) and the rear side of the tooth (on the right in FIG. 1B) more or less the rolling contour of the gingiva 9, which forms a collar around the tooth. The progression of the cemento-enamel junction SZG is depicted in FIG. 1B by a curve which is bulged upwards. The progression of the bone level is illustrated in dashed form in the side view of FIG. 1B by a further curve which is bulged upwards, wherein the maximum of this curve is denoted as bone level KN2. The progression of the cemento-enamel junction SZG is depicted in FIG. 1C by a curve which is bulged downwards. The progression of the bone level is illustrated in dashed form in the view of FIG. 1C by a further curve which is bulged downwards, wherein the minimum of this curve is denoted as bone level KN1. For the sake of a simplified presentation, in case of the schematic illustration of FIG. 1B the level of the cemento-enamel junction SZGN1 at the front- and rear side of the tooth FZ: 11 are at the same height. That is, the line, which reproduces the level of the cemento-enamel junction SZGN1, is running horizontally. However, the level of the cemento-enamel junction SZGN1 and the contour of the gingiva 9 typically are lying at a different height at the front of a tooth and at the rear side of a tooth, that is, the line, which reproduces the level of the cemento-enamel junction SZGN1, is mostly inclined in practice. The inclined progression of the level of the cemento-enamel junction SZGN1 is exemplarily depicted in FIG. 5A by means of a dashed reference line.

Correspondingly, the level NA (A stands for outside=vestibular) differs from the level NI (I stands for inside=oral) at the abutment basis 102 of the invention, as can be seen in FIG. 5A. Hence, an asymmetry of the shape of the cross section and a specially directed orientation (angular position) result which have to be observed when fixing the abutment bass 102 on the implant 103.

The asymmetry of the shape of the cross section can be recognized in FIG. 5A on the basis of a first abutment 102, it is, however, to be mentioned that FIG. 5A does not show a cross section but a side view. The abutment basis 102 is shown in FIGS. 5A through 5C with the same orientation as the tooth FZ: 11 in FIG. 1B.

Figure 2A:
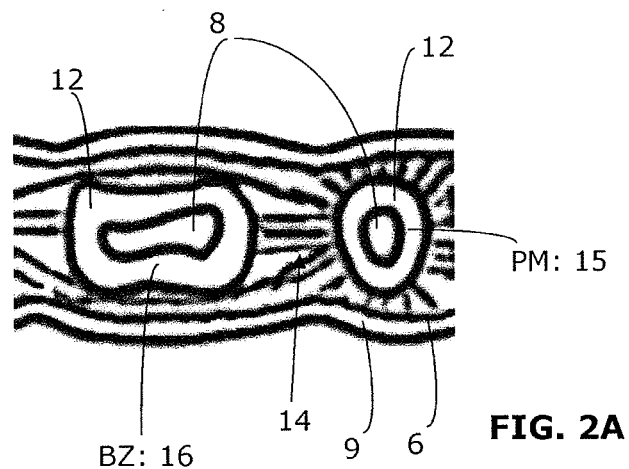
FIG. 2A shows a strongly schematized sectional view of a premolar PM: 15 and a molar BZ: 16 of the upper jaw of a human dentition including the surrounding soft tissue morphology from below.
Figure 2B:
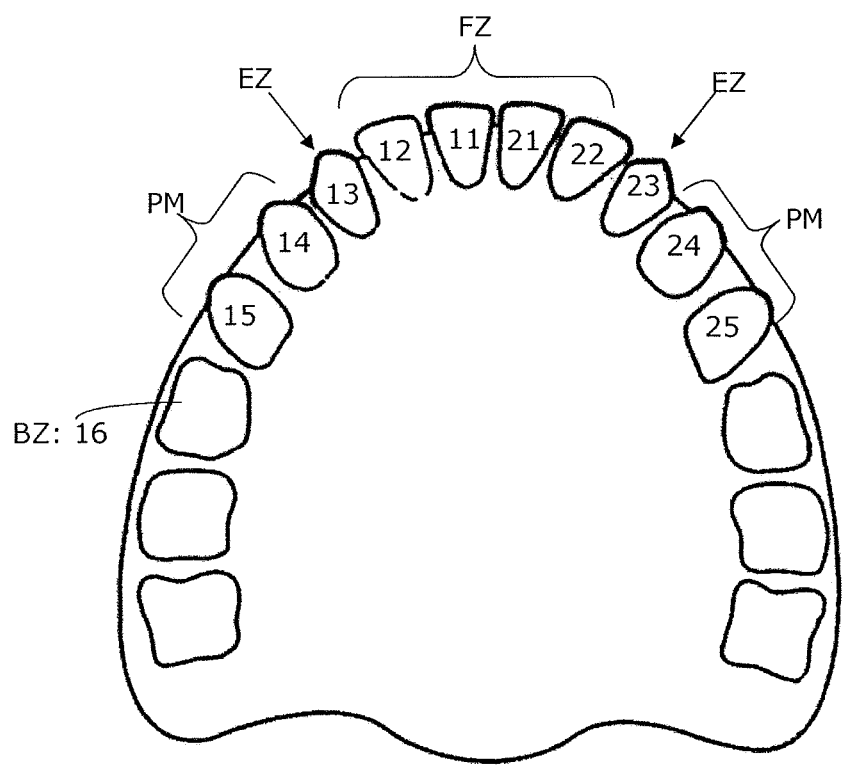
FIG. 2B shows a schematic view of a human upper jaw from below.
Figure 3A:
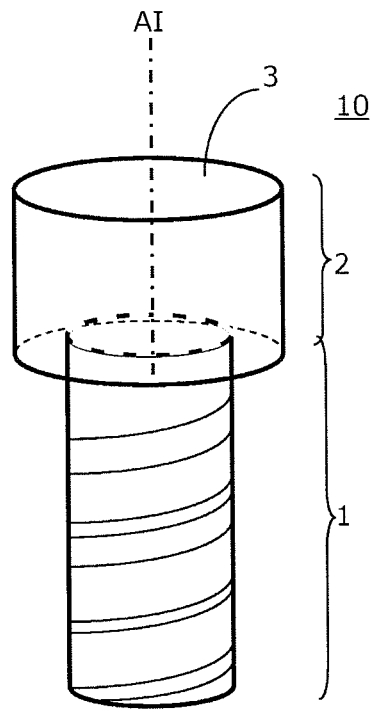
FIG. 3A shows a strongly schematized perspective view of an implant system in accordance with the invention comprising an implant with parallel walls and an abutment mounted thereon.
Figure 3B:
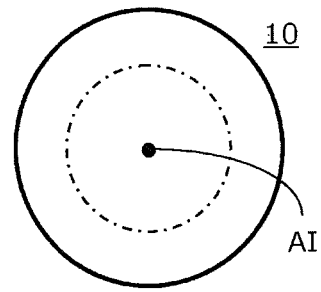
FIG. 3B shows a strongly schematized top view of the implant systems according to FIG. 3A.
Figure 3C:
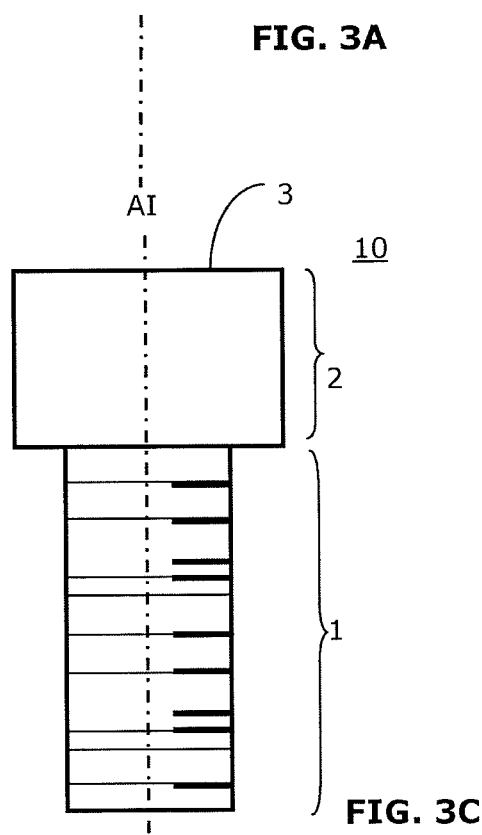
FIG. 3C shows a strongly schematized side view of the implant systems according to FIG. 3A.
Figure 4:
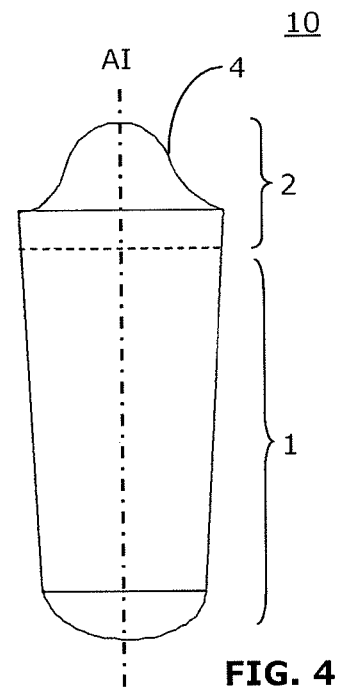
FIG. 4 shows a schematic side view of one-piece, scalloped rotationally symmetric dental prosthesis according to prior art.

It can be recognized in FIG. 2B in outlines that each tooth has another typical cross section respectively foot print. The premolars (e.g. the teeth PM: 14 and PM: 15 pursuant to the FDI-scheme) typically have an oval cross section (for instance like the shape of the foot print Q1 in FIG. 8), the canine teeth EZ (e.g. the tooth EZ: 13 pursuant to the FDI-scheme) typically have a deltoid cross section with rounded corners (for instance like the shape of the foot print Q2 in FIG. 8) and the anterior teeth (e.g. the teeth FZ: 11 and FZ: 12 pursuant to the FDI-scheme) typically also have a deltoid cross section with rounded corners (for instance like the shape of the foot prints Q3 and Q4 in FIG. 8).

Figure 9:
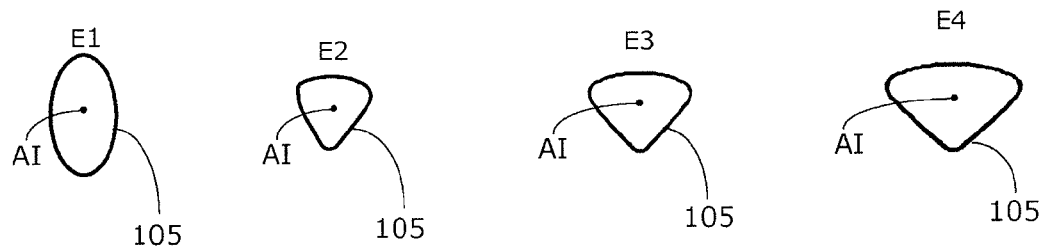
FIG. 9 shows a strongly schematized view of the foot print of four typical abutments shapes and sizes.

Investigations have revealed that the variety of shapes and the variations re shape and dimensional difference in case of anterior and premolar teeth is very little only. It is thus, in accordance with the invention, possible to offer three or four industrially produced abutment basis 102 (as indicated in FIG. 9) in order to be able to make for almost all cases a replacement for a human anterior tooth FZ or premolar PM.

Figure 8:
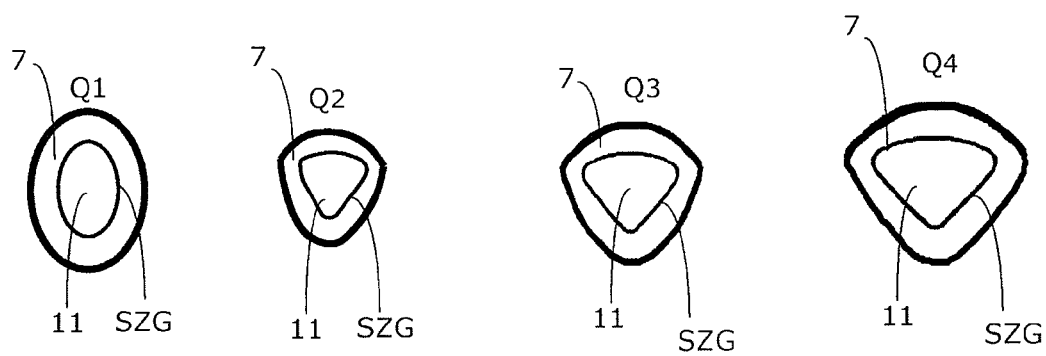
FIG. 8 shows a strongly schematized side view of the typical shapes and sizes of teeth viewed from below (foot print)

The respective abutment basis 102 of the invention approximately have, if viewed from the top, the contour and dimension of the cemento-enamel junction SZG of the corresponding shapes Q1, Q2, Q3, and Q4, as schematically illustrated in FIG. 8. Four possible shapes of foot prints and dimensions (projected into the plane of the drawing) of the abutment basis 102 are schematically shown and designated as E1 through E4 in FIG. 9. The shape of foot print E1 has an oval or slightly ovoid shape. An abutment basis 102 pursuant to the shape of foot print E1 preferably has a dimension of 4.5 mm times 6 mm and is suitable for making a dental prosthesis of a premolar. The shape of foot prints E2, E3, and E4 have deltoid shapes. An abutment basis 102 pursuant to the shape of foot print E2 preferably has a diameter of 4 mm, an abutment basis 102 pursuant to the shape of foot print E3 preferably has a diameter of 5 mm and an abutment basis 102 pursuant to the shape of foot print E4 preferably has a diameter of 6 mm. The shapes of foot prints E2, E3, and E4 are especially suitable for making a dental prosthesis of a canine or anterior tooth. The circumferential ridge/shoulder 105 defines the shapes of foot prints E2, E3, and E4 if viewed from above respectively in the projection into the plane of the drawing. None of the shapes of foot prints E1, E2, E3, and E4 is rotationally symmetric with respect to the implant axis A1, which in FIG. 9 stands perpendicular on the plane of the drawing, respectively.

It can be determined for instance by means of a local examination of the extraction channel and/or the extracted tooth and/or by means of imaging methods which type and which size of the inventive abutment basis 102 is suitable in order to build up a dental prosthesis. When choosing the type and size of the abutment basis 102 preferably also the position and thickness of the connective tissues 6 above the jawbone 5 (if viewed from crestal direction) is determined (see FIG. 1B and FIG. 1C). In this context values for the thickness respectively position of the mesial (in the direction of the jaw center line), distal (remote from the jaw center line), vestibular (towards the outside) and palatial (pointing towards the palatine) connective tissue 6 can be considered.

The invention does not focus on abutment basis individually produced for patients but on ready-made abutment basis 102. In order to enable optimum solutions nevertheless, an implant system 100 of all embodiments preferably comprises different (preferably at least three) abutment basis 102 with the shapes E1, E2, E3, and E4 (see FIG. 9) so that the surgeon in each case has a suitable abutment basis 102 at hand, the shape and size of which approximately corresponds to the local situation after the extraction of a tooth.

Such an implant system 100 preferably comprises in all embodiments at least one abutment basis 102 which has an elliptic shape of the foot print similar to E1 viewed in a horizontal section, an abutment basis 102, and at least one roundish-deltoid shape of the foot print similar to E2 and/or E3 and/or E4.

The shapes of the foot prints E1-E4 of the abutment basis 102 for that matter are adapted to the shapes of the foot prints Q1-Q4 of an anterior tooth FZ, canine tooth EZ or premolar tooth PM to be replaced by a dental prosthesis.

An abutment basis 102 of the invention of all embodiments comprises, if viewed from the bottom to the top, at least the following characteristic:

A first interface 107; preferably there is a proximal interface plane 109, which in the mounted state runs parallel (plane on plane) with respect to a distal surface 110 of the implant 103. The interface plane 109 lies perpendicular with respect to the implant axis AI and it is essentially planar. Preferably, there also is a connecting post for an inner or outer implant connection 115, as is exemplarily and schematically shown in FIG. 5A.

A concave cladding area 111, which provides for a harmonic (free of edges) transition from the interface plane 109 to a circumferential ridge/shoulder 105. The face of the cladding area 111 is hatched in FIG. 5A in order to bring it out optically.

A circumferential ridge/shoulder 105, which in the projection into a plane that is perpendicular to the drawing plane of FIG. 5A, corresponds to or approximates one of the shapes of the foot prints E1, E2, E3 or E4 of FIG. 9. In an interdental side view the circumferential ridge/shoulder 105 has the scalloped progression shown in FIG. 5A, whereby the level NA (A stands for outside) can be different from the level NI (I stand for inside). The circumferential ridge/shoulder 105 has a curve shape which is bulged downwards, as can be seen in FIG. 5D.

A distal, scalloped surface 104 which in the projection into a plane that is perpendicular with respect to the drawing plane of FIG. 5A corresponds to or approximates one of the shapes of the foot prints E1, E2, E3 or E4 of FIG. 9.

Reference lines and information can be seen in FIG. 5B which permit the shape and dimension of the abutment basis 102 to be better described. The interface plane 109 lies in a plane F1 that is perpendicular with respect to the implant axis AI. The distance a1 (in parallel to the implant axis AI) between the plane F1 and the plane F2 of all embodiments preferably is between 2 mm and 8 mm depending on the abutment basis 102. The distance a2 (in parallel to the implant axis AI) between the plane F2 and the plane F3 of all embodiments preferably is between 0.3 mm and 5 mm depending on the abutment basis 102. The circumferential ridge/shoulder 105 preferably has a thickness d1 (in parallel to the implant axis AI) in the palatine and vestibular region of the abutment 102 which is between 0.1 mm and 0.6 mm. The thickness of the circumferential ridge/shoulder 105 in the region of the apex 112 of the abutment basis 102 corresponds to the distance a2 mentioned.

The radial axial distance ra between the implant axis AI and the outer most circumference of the interface plane 109 of all embodiments preferably is between 1.5 mm and 3 mm. It is to be observed that the interface plane 109 of all embodiments preferably is designed circularly and concentric with respect to the implant axis AI.

The maximum radial distance rmax between the implant axis AI and the outer circumference of the ridge/shoulder 105 of all embodiments preferably is between 2 mm and 5 mm. It is to be observed that the implant axis AI preferably lies in the center of the ovoid or deltoid shapes E1, E2, E3, E4.

Preferably, all abutment basis 102 of the invention have a total height a1+a2 which is 10 mm at most. Typically the total height a1+a2 is even smaller than 6 mm.

Preferably, the abutment basis 102 of the invention have a maximum diameter, which is 10 mm at most. Typically the maximum diameter is smaller than 6 mm.

The described concave cladding area 11 of all embodiments provides for a smooth (that is free of steps) transition between the rotationally symmetric interface plane 109 and the non-symmetric circumferential ridge/shoulder 105 respectively the non-symmetric scalloped surface 104.

One can see in the side view of FIGS. 5A and 5B that the cross section is designed asymmetrically with respect to the implant axis AI, that is the respective part of the abutment basis 102 which lies on the right hand side of the implant axis AI does not have a mirror symmetry with respect to the part of the abutment basis 102 which lies on the left hand side of the implant axis AI. The concavity on the vestibular side (curve 114) and the concavity on the palatine side (curve 113) are considerably distinct.

The apex 112 of the abutment basis 102 of the invention does not have to lie on the implant axis AI in case of all embodiments, as is the case in the example which is shown in FIGS. 5A and 5B.

Figure 6B:
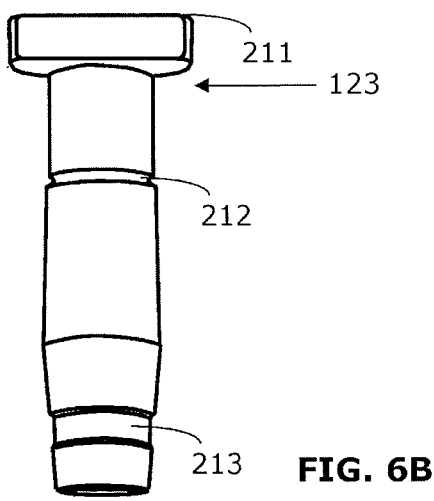
FIG. 6B shows a side view of a prosthetic post for attachment on an inventive abutment basis.
Figure 6C:
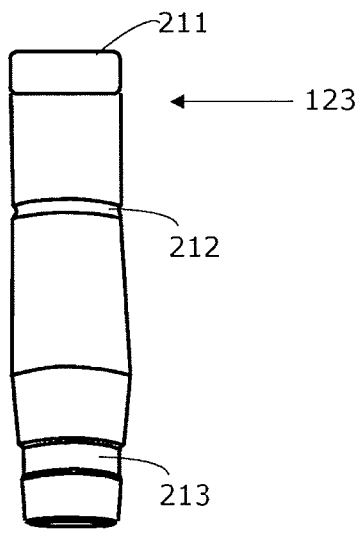
FIG. 6C shows a side view rotated by 90 degrees of the prosthetic post of FIG. 6B.

FIG. 5C shows a miniaturized side view of the first abutment basis 102 of FIG. 5A together with a prosthetic post 210 placed on top, which is coaxially connected (e.g. screwed on) to the abutment basis 102 with respect to the implant axis AI. The prosthetic post 210 comprises an interface (here called interface 123) which serves for attaching/fixing a crown 122 or a supra construction. A head or a plate 211 can for instance be provided at the prosthetic post 210, as can be seen in FIGS. 5C, 6B, and 6D. In FIG. 6B it can be seen that the head or plate 211 protrudes beyond the diameter of the prosthetic post 210. The head or plate 211 can be flattened on the side, as can be seen in FIG. 6C. circumferential notches 212, 213 can be provided at the prosthetic post 210 in order to be able to clamp or to screw tightly (e.g. with a stud screw) the prosthetic post 210.

Figure 7:
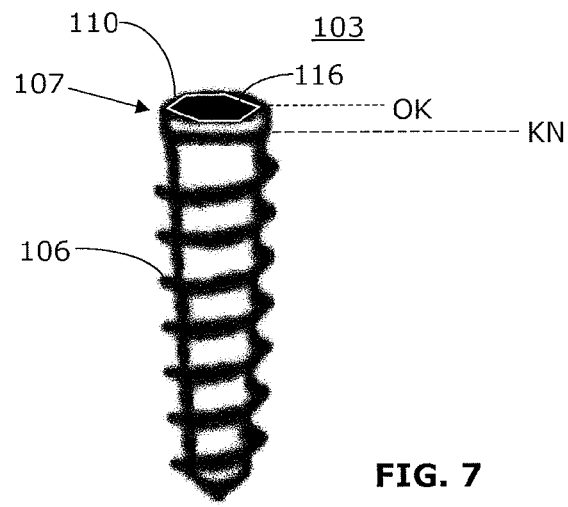
FIG. 7 shows a strongly schematized perspective view of an exemplary implant in accordance with the prior art, which can be used in connection with the present invention.

Preferably, all embodiments of the abutment basis 102 comprise a connecting post for an inner or a receiving opening for an external implant connection 115, which can be seen in FIGS. 5A, 5B, 5C, and 5D. The connecting post can be polygonal and/or rotationally symmetrically conical. This connecting post 115 respectively the receiving opening serve as interface with the implant 103. If such a connecting post 115 is provided at the abutment basis 102, the implant 103 comprises a corresponding, appropriately designed receiving opening 116 (internal connection). In FIG. 7 this receiving opening 116 is purely schematically indicated by a black hexagon. In FIG. 5A this receiving opening 116 is shown by a dashed line.

There are already many different (standard) interfaces 107 in order to enable an abutment basis 102 to be connected with an implant 103. Most of the Interfaces employed today are designated, depending on the constellation, internal hex-interface (as shown in FIGS. 5A, 5B, and 6A), external hex-interface, standard hex-interface, slim hex-interface, wide hex-interface etc.

Established interfaces are for instance known from the documents U.S. Pat. No. 4,960,381, U.S. Pat. No. 5,407,359, U.S. Pat. No. 5,209,666, and U.S. Pat. No. 5,110,292. These prior known solutions can be used in connection with all embodiments of the present invention.

After having chosen a suitable abutment 102, this is connected to the implant 103 so that the circumferential ridge/edge 105 which runs asymmetrically around the abutment 102 as much as possible has about the same distance in all directions (mesial, distal, vestibular and palatine) with respect to the jawbone 105 and an even position with respect to the connective tissue 6.

Preferably, the abutment basis 102 of all embodiments have a pronounced circumferential ridge/shoulder 105, as can be seen in FIG. 5A, for instance. The circumferential ridge/shoulder 105 approximately follows the area of the largest diameter/circumference of the abutment basis 012 viewed in the horizontal.

The abutment basis 102 of the invention is in about approximated to the asymmetric scalloped shape and progression of the cemento-enamel junction SZG. The abutment basis 102 thus also has an asymmetric scalloped shape and the abutment basis 102 is connected to the implant 103 so that the orientation of the scalloped surface 104 of the abutment basis 102 essentially corresponds to the position of the cemento-enamel junction SZG of the tooth prior to the extraction. For this reason that angular position (index positioning) of the abutment basis 102 with respect to the implant 103 is important. The (hex-) interface 107 thus plays an important role since it enables a rotation of the abutment basis 102 about the implant axis AI relative to the fixedly implanted implant 103.

After the abutment basis 102 was placed on the implant 103 in the right angular position (index position) and connected therewith (e.g. by means of a set screw or a screw 120, as shown in FIG. 5A), a temporary crown can be fixed on the abutment basis 102 e.g. using a known glue or cement, until a final crown 122 (see FIG. 10B) is available. Preferably, the mentioned prosthetic post 210 is employed for fixing the crown 122 or a supra construction. These steps are sufficiently known and are thus not explained further.

Figure 10A:
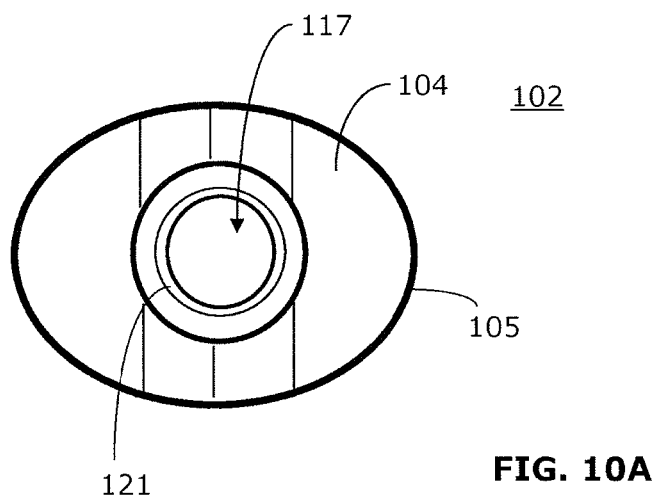
FIG. 10A shows a strongly schematized top view of a further abutment basis of the invention, which has an oval foot print.

In order to enable the connecting of the abutment basis 102 with the implant 103, the abutment basis 102 preferably comprises a through hole 117 and the implant 103 a screw hole 118 with internal thread, as schematically illustrated in FIG. 5A by means of an example. The through hole 117 and the screw hole 118 extend coaxially with respect to the implant axis AI. Due to this a set screw or a screw 120 can be screwed in from above into the screw hole 118 in order to fix the abutment 102 on the implant 103. The through hole 117 preferably has a collar or a reduction of the diameter 121 lying inside so that a head 119 of the screw 120 can rest thereon. This kind of connection of the abutment basis 102 with the implant 103 can be used in all embodiments. However, there are also other approaches which can be used. It is important that the prosthetic post 210 can be inserted into the abutment basis 102 from above and fixed there. In case of correspondingly designed implant systems 100 the through hole 117 can be seen in a top view of the scalloped surface 104 of the abutment basis 102, as shown in FIGS. 6A and 10A. Depending on the orientation, the through hole 117 can also be seen in a side view of the abutment basis 102 (see FIG. 5D).

In FIG. 6A a top view of an abutment basis 102 having a slightly deltoid shape is shown. In the top view the through hole 117 as well as the collar or a reduction of the diameter 121 can be seen. In FIG. 10A, however, the top view of an abutment basis 102 is shown which has an ovoid shape. In the top view the through hole 117 as well as the collar or a reduction of the diameter 121 can be seen.

Preferably, the inventive implant system 100, which comprises at least one abutment basis 102, the (standard-) implant 103 and the prosthetic post 210, is implanted a short time after the extraction of a tooth (e.g. an anterior tooth FZ) in order not to permanently "disturb" the surrounding tissue- and bone structures. In this context care is taken that contrary to the doctrine the unit of implant 103 and abutment basis 102 is fixed in the bone so that the scalloped surface 104 of the abutment basis 102 is lying supracrestally at approximately 1.5 mm. An exemplary standard implant 103 with a conically shaped base body is shown in FIG. 7 whereby the implant 103 comprises an outer thread and a mechanical interface 107 for connection with the abutment basis 102 of the invention.

The implant 103 in all embodiments can either have parallel walls or a conical (root shaped) base body. In FIG. 5A an implant 103 with a parallel wall base body in indicated by means of hashed lines. In FIG. 7, however, an implant 103 with a conical base body is schematically illustrated. The type/shape of the implant 103 is to be considered when providing the required drill holes in the jawbone 5.

One can also temporarily screw on/clip on an impression post on the abutment basis 102 which in the broadest sense inside the patient's mouth corresponds to the negative occlusal surface profile of the abutment (profile in the top view). However, the prosthetic post can also serve as impression post. It is important that the seat of the impression post is precisely defined with respect to the abutment bass 102 in the three-dimensional observation.

The abutment basis 102 in all embodiments comprises a biocompatible material, preferably titanium, a titanium alloy and zirconium oxide, or its combinations, and it can, if desired, be coated with titanium-zirconium ceramic and/or titanium-niobium-oxide nitride ceramic, for example. The surface of the abutment basis 102 can however also be polished, machined, etched or laser-treated or coated with bio-active material. According to requirements, the surface morphology can be designed so that the attachment of soft tissue (cellular and/or fibrous elements) is supported.

Preferably in all embodiments an implant 103 is employed which has a chamfered edge 108 in the region of the interface 107, which runs around 360 degrees. An implant 103 with chamfer 108 on the distal upper side 110 is indicated in FIG. 5A. The upper side 110 of the implant 103 in these cases is not completely flat.

An implant system 100 with such an implant 103 with chamfer 108 and one or more abutment basis 102 is particularly advantageous over hitherto existing implant solutions especially because an overall waisted constellation results because of the chamfer 108 and the special concave shaped cladding area 111.

Figure 10B:
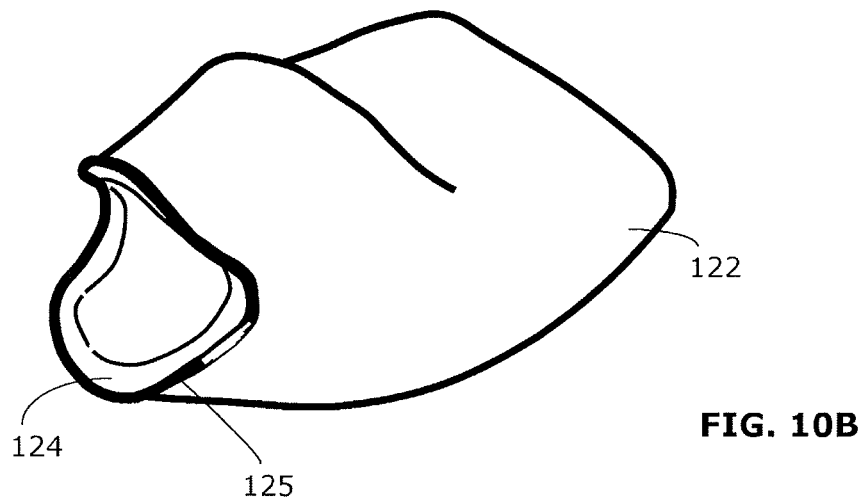
FIG. 10B shows a strongly schematized perspective view of a crown, which is constructed for mounting on an abutment basis of FIG. 10A.

A strongly schematized top view of a further abutment basis 102 of the invention which here has an oval foot print is shown in FIG. 10A. FIG. 10B shows a schematic perspective view of a crown 122 which is designed for attaching it on the abutment basis 102 of FIG. 10A. In FIG. 10B the crown 122 is lying with the front side of the tooth (tooth front) on a support. In FIG. 10B the rear side of the crown 122 is visible. One can recognize that the crown 122 comprises a complementary inner shape 124 which is exactly adapted to the shape and dimension of the abutment basis 102 of FIG. 10A. The crown 122 has a circumferential border 125 which approximately corresponds to the circumferential ridge/shoulder 105 of the abutment basis 102. The scalloped surface 104 of the abutment basis 102 sits inside the crown 122 when fixing the crown 122 on the abutment basis 102 and the circumferential border 125 sits tight on the circumferential ridge/shoulder 105 of the abutment basis 102.

REFERENCE SIGNS

| | |
|---|---|
| Implant (post-shaped section) | 1 |
| abutment | 2 |
| Flat surface | 3 |
| Scalloped surface | 4 |
| Jawbone | 5 |
| Connective tissue | 6 |
| Dental enamel | 7 |
| Nerve | 8 |
| Gingiva (Epithel) | 9 |
| Dental prosthesis-implant | 10 |
| Dentin | 11 |
| Root of the tooth | 12 |
| Paradont | 13 |
| Collagen fibers | 14 |
| interdental facial papilla | 15 |
| incisors | FZ: 11, FZ: 12 |
| incisors | FZ: 21, FZ: 22 |
| Canine teeth | EZ: 13, EZ: 23 |
| Premolar | PM: 14, PM: 15 |
| Premolar | PM: 24, PM: 25 |

-continued

| | |
|---|---|
| Implant system (Dental prosthesis-implant) | 100 |
| post-shaped section | 101 |
| Abutment basis | 102 |
| Implant | 103 |
| Scalloped surface | 104 |
| Circumferential ridge/shoulder | 105 |
| Outer thread | 106 |
| 1. interface | 107 |
| chamfer/reduction of diameter | 108 |
| interface plane | 109 |
| Upper side | 110 |
| Concave cladding area | 111 |
| Apex | 112 |
| curve | 113 |
| curve | 114 |
| Connecting post/implant connection | 115 |
| Receiving opening | 116 |
| Through hole | 117 |
| Screw hole | 118 |
| Screw head | 119 |
| Set screw or screw | 120 |
| Collar or reduction of the diameter | 121 |
| crown | 122 |
| 2. interface | 123 |
| Complementary inner shape | 124 |
| circumferential boarder | 125 |
| Abutment system | 200 |
| prosthetic post | 210 |
| Head or plate | 211 |
| notch | 212 |
| notch | 213 |
| distance | a1 |
| Implant axis | AI |
| Molar tooth | BZ |
| thickness | d1 |
| foot print (in projection) | E1, E2, E3, E4 |
| Canine tooth | EZ |
| layers | F1, F2, F3 |
| Bone level | KN1, KN2 |
| Level inside (oral) | NI |
| Level outside (vestibular) | NA |
| Upper edge | OK |
| Premolar | PM |
| Cross-sections | Q1, Q2, Q3, Q4 |
| incisor | FZ |
| cemento-enamel junction | SZG |
| Level of the cemento-enamel junction | SZGN1; SZGN2 |

The invention claimed is:

1. An abutment system for use in an area of anterior teeth and premolar teeth, said system comprising:
    an abutment basis comprising:
        a first interface comprising an interface plane adapted to overlie an implant;
        a scalloped upper surface with an apex and that is asymmetric relative to an axis concentric and perpendicular to the interface plane;
        a three-dimensional shape that is asymmetrical relative to the axis; and
        a concave cladding area arranged between the first interface and the scalloped upper surface and providing a harmonic transition from the first interface; and
    a separate prosthetic post which is attachable to a region of the scalloped upper surface, said prosthetic post, when in a mounted state, extending coaxially with respect to the axis.

2. The system of claim 1, further comprising a second interface located above the scalloped upper surface and being configured for attaching a prosthetic element.

3. The system of claim 1, wherein the abutment basis further comprises:
    a through hole arranged in a region of the scalloped upper surface for attaching the prosthetic post, said through hole extending essentially parallel to or coaxial with the axis.

4. The system of claim 1, wherein the abutment basis comprises, when viewed horizontally, one of:
    an elliptical shaped foot print; or
    a rounded deltoid shaped foot print.

5. The system of claim 1, wherein the abutment basis comprises, when viewed horizontally, a foot print shaped to resemble one of:
    an incisor tooth;
    a canine tooth; or
    a premolar tooth.

6. The system of claim 1, wherein the first interface is configured to be rotated and locked in position between at least three different index positions relative to the axis.

7. The system of claim 1, wherein the abutment basis further comprises one of:
    a connecting post located below the first interface and configured to connect to an inner implant connection, or
    a receiving opening for an external implant connection.

8. The system of claim 1, wherein the first interface is one of:
    a hex-interface;
    a surface coupled to an hex-shaped implant connection; or
    a surface that allows for six different index positions with respect to the axis.

9. The system of claim 1, wherein the abutment basis is capable of being implanted in a mucous area either immediately or delayed.

10. The system of claim 1, wherein the abutment basis and the prosthetic post are connected via a screw connection, whereby the prosthetic post is positioned supragingival after connection.

11. The system of claim 1, further comprising another abutment basis, wherein the abutment basis and the another abutment basis have different foot print shapes and/or different sizes.

12. A dental prosthesis-implant comprising:
    an abutment system comprising;
        an abutment basis comprising:
            a first interface comprising an interface plane adapted to overlie an implant;
            a scalloped upper surface with an apex and that is asymmetric relative to an axis concentric and perpendicular to the interface plane;
            a three-dimensional shape that is asymmetrical relative to the axis; and
            a concave cladding area arranged between the first interface and the scalloped upper surface and providing a harmonic transition from the first interface; and
        a separate prosthetic post which is attachable to a region of the scalloped upper surface, said prosthetic post, when in a mounted state, extending coaxially with respect to the axis; and
    a separate implant comprising:
        a base body which is essentially rotationally symmetric with respect to the axis; and
        an outer thread.

13. The prosthesis-implant of claim 12, wherein the abutment basis is connectable to the implant via a screw thread.

14. The prosthesis-implant of claim 12, wherein the implant comprises:

a central bore that is coaxial with respect to the axis; and
an inner thread for receiving a threaded rod or a screw.

15. The prosthesis-implant of claim 12, wherein the implant comprises:
   a circumferential chamfer located adjacent the first interface and being configured to promote, after implantation, bone attachment and/or tissue attachment.

16. The prosthesis-implant of claim 12, wherein the implant comprises:
   a reduced diameter upper surface configured to abut directly or be spaced by a distance from the first interface, said first interface being a flat proximal interface plane.

17. The prosthesis-implant of claim 12, wherein, after implantation, the scalloped upper surface is configured to lay supracrestally.

18. An abutment system for use in an area of anterior teeth and premolar teeth, said system comprising:
   an abutment member comprising:
      an interface surface comprising an interface plane adapted to overlie an implant;
      an upper surface having an apex arranged between concave surfaces that are asymmetric relative to an axis concentric and perpendicular to the interface plane;
      a fastener opening;
      a three-dimensional shape that is asymmetrical relative to the axis; and
      a concave peripheral region arranged between the interface surface and the upper surface; and
   a prosthetic post which is attachable to a region of the upper surface, said prosthetic post, when in a mounted state, extending coaxially with respect to the implant axis.

19. An abutment system for use in an area of anterior teeth and premolar teeth, said system comprising:
   an abutment member comprising:
      an interface surface comprising an interface plane adapted to overlie an implant;
      an implant connection extending from the interface surface;
      an asymmetric upper surface having an outwardly curved region located between inwardly curved regions;
      a central through opening;
      a three-dimensional shape that is asymmetrical relative to an axis concentric and perpendicular to the interface plane; and
      a concave peripheral region extending to the interface surface and arranged between the interface surface and the upper surface; and
   a prosthetic post which is attachable to a region of the upper surface, said prosthetic post, when in a mounted state, extending coaxially with respect to the axis.

20. The system of claim 19, wherein the implant connection is one of:
   hex-shaped; or
   non-circular in shape.

* * * * *